(12) United States Patent
Floor

(10) Patent No.: US 7,628,086 B2
(45) Date of Patent: Dec. 8, 2009

(54) APPARATUS AND METHOD FOR TAKING GASEOUS SAMPLES

(75) Inventor: Karsten Brink Floor, Hadsund (DK)

(73) Assignee: FLS Airloq A/S, Valby (DK)

(*) Notice: Subject to any disclaimer, the term of this patent is extended or adjusted under 35 U.S.C. 154(b) by 99 days.

(21) Appl. No.: 11/568,031

(22) PCT Filed: Apr. 21, 2005

(86) PCT No.: PCT/DK2005/000279

§ 371 (c)(1),
(2), (4) Date: Dec. 6, 2006

(87) PCT Pub. No.: WO2005/103643

PCT Pub. Date: Nov. 3, 2005

(65) Prior Publication Data

US 2007/0180893 A1  Aug. 9, 2007

(30) Foreign Application Priority Data

Apr. 22, 2004 (DK) .................. PA 2004 00640

(51) Int. Cl.
*G01N 1/20* (2006.01)
(52) U.S. Cl. .................................................. 73/864.24
(58) Field of Classification Search .............. 73/863.23, 73/863.24, 1.06
See application file for complete search history.

(56) References Cited

U.S. PATENT DOCUMENTS

| 4,161,883 | A | * | 7/1979 | Laird et al. | 73/863.24 |
| 4,379,412 | A | | 4/1983 | Wood | 73/863.24 |
| 4,484,481 | A | * | 11/1984 | Laird et al. | 73/863.12 |
| 4,738,147 | A | | 4/1988 | Tomlin | 73/864.81 |
| 5,490,429 | A | | 2/1996 | Jarolics et al. | 73/863.83 |
| 2003/0110950 | A1 | | 6/2003 | Sjostrom et al. | 96/413 |
| 2005/0084976 | A1 | * | 4/2005 | Baldwin et al. | 436/81 |

FOREIGN PATENT DOCUMENTS

| EP | 0530684 | | 3/1993 |
| FR | 2715732 | | 8/1995 |
| GB | 1525336 | | 9/1978 |
| JP | 06201277 A | * | 7/1994 |
| JP | 2003130769 A | * | 5/2003 |
| WO | WO 9528628 A1 | * | 10/1995 |
| WO | WO 9712658 | | 4/1997 |

* cited by examiner

*Primary Examiner*—Hezron Williams
*Assistant Examiner*—Tamiko D Bellamy
(74) *Attorney, Agent, or Firm*—Darby & Darby P.C.

(57) ABSTRACT

An apparatus and a method for taking out samples of a gaseous medium containing particles, the apparatus comprising a pipe having one end adapted for introduction into the gaseous medium, a tubular filter positioned coaxially with the pipe, a removable closure positioned on the down stream side of the tubular filter, means for removing filtered gas from the outside of the tubular filter and separate blow back means in communication with the outer side of the tubular filter.

9 Claims, 3 Drawing Sheets

11    2

APPARATUS AND METHOD FOR TAKING GASEOUS SAMPLES

CROSS-REFERENCE TO PRIOR APPLICATION

This is a U.S. National Phase Application under 35 U.S.C. §371 of International Patent Application No. PCT/DK2005/000279 filed Apr. 21, 2005, which claims priority of Denmark Patent Application No. PA200400640 filed Apr. 22, 2004, both of which are hereby incorporated by reference. The International Application published in English on Nov. 3, 2005 as WO 2005/103643 A1 under PCT Article 21(2).

FIELD OF INVENTION

This invention relates to an apparatus for taking samples of a gaseous medium containing solid particles, said apparatus comprising a pipe having one end adapted for introduction into said gaseous medium, a tubular filter for filtering off the solid particles, said filter being positioned coaxially with the pipe and communicating with the interior of the pipe, and means for withdrawing filtered gaseous medium from the outer side of the tubular filter.

BACKGROUND FOR THE INVENTION

In production processes involving a high fuel consumption, such as the processes in a cement production plant, it is important to know the composition of the gasses present during the process. The knowledge of the composition of the gasses is important in order to optimize the combustion process, to prohibit dangerous process situations, to reduce emission and to improve the quality of the product.

The temperature within a rotary kiln used for the production of cement is typically of the order of 1300° C. and sometimes even above 1500° C. and the combustion gasses have a dust content of up to 3000 g/Nm$^3$. These harsh conditions set serious demands to the equipment used for measuring the composition of the combustion gasses which has to be able to withstand the temperature as well as dealing the high dust content.

Normally the composition of the process gases is determined by taking out a small sample and analyzing said sample. This procedure is complicated by the fact that the composition of the gasses changes over time and with temperature changes. Thus it is important to be able to get the sample fast from the process to the sensors determining the composition but at the same time the dust must be separated from the gas to be analyzed.

Previous attempts to solve this problem all have disadvantages. It has been tried to withdraw the sample of the dust-containing gaseous medium through a filter placed in a pipe being introduced into the combustion chamber or by using a filter placed outside in a housing. This results in the inevitable clogging of the filter and in a manner which makes it very difficult to clean the filter and further there is a risk that the particles remain in the pipe and cools/influences the new samples or even worse the particles begins to calcinate. Also visual inspection of the pipe is prohibited by the filter or the filter itself has to be removed prior to inspection. Inspection of such an arrangement takes up to 2 hours.

Another approach has been to withdraw a stream of dust containing gaseous medium from a combustion chamber, passing said stream through a filter device comprising a tubular filter and continuously recycling the flow to the combustion chamber. Samples of dust free gaseous medium are obtained by withdrawing gaseous medium from a zone surrounding the tubular filter. This approach gives a heavy wear and tear due to the large amount of hot dust flowing through the system.

Thus there is a need for an apparatus and a method for taking out gas samples from medium containing solid particles which do not have the drawbacks of the prior art.

According to the invention there is provided an apparatus for taking samples of a gaseous medium containing solid particles, said apparatus comprising a pipe having one end adapted for introduction into said gaseous medium, a tubular filter for filtering off the solid particles, said filter being positioned coaxially with the pipe and communicating with the interior of the pipe, a removable closure being positioned on the downstream side of the tubular filter and coaxially with the pipe and withdrawal means for withdrawing the filtered gaseous medium from the outer side of the tubular filter, the apparatus being characterized in that it further comprises separate blow back means in communication with the outer side of the tubular filter.

According to another aspect of the invention there is provided an apparatus for taking samples of a gaseous medium containing solid particles, said apparatus comprising a pipe having one end adapted for introduction into said gaseous medium, a tubular filter for filtering off the solid particles, said filter being positioned coaxially with the pipe and communicating with the interior of the pipe, a removable closure being positioned on the downstream side of the tubular filter and coaxially with the pipe and withdrawal means for withdrawing the filtered gaseous medium from the outer side of the tubular filter, the apparatus being characterized in that the pipe has cooling means for cooling the end adapted for introduction Into the gaseous medium.

According to another aspect of the invention there is provided an apparatus for taking samples of a gaseous medium containing solid particles, said apparatus comprising a pipe having one end adapted for introduction Into said gaseous medium, a tubular filter for filtering off the solid particles, said filter being positioned coaxially with the pipe and communicating with the interior of the pipe, a removable closure being positioned on the downstream side of the tubular filter and coaxially with the pipe and withdrawal means for withdrawing the filtered gaseous medium from the outer side of the tubular filter, the apparatus being characterized in that the removable closure comprises an access port positioned coaxially with the pipe.

The apparatus of the invention operates as follows:

When the one end of the pipe is introduced into the gaseous medium from which samples are to be taken the means for withdrawing filtered gaseous medium from the outer side of the tubular filter will cause a slow of gaseous medium containing suspended solid particles to pass through the pipe and the tubular filter and to form a layer of solid particles on the inner side of the tubular filter.

At intervals the access port in the closure on the downstream side of the tubular filter is opened thus allowing the interior side of the pipe and the filter to be inspected. Preferably the access port further comprises a quick connector thus allowing for blow back of gas through the pipe during cleaning.

The layer of solid particles formed on the inner side of the filter may be removed when appropriate by discontinuing the withdrawal of gaseous medium form the outer side of the tubular filter and by passing a stream of gaseous medium such as air from the outer side of the filter and into the pipe as explained in more details below.

The end adapted for being introduced into the gaseous medium is either permanently in the gaseous medium or as preferred the pipe is mounted in a slidable member and the moved into the gaseous medium when the samples are taken.

Due to the high temperatures present in a kiln it is often necessary to cool the end adapted for introduction into the gaseous medium, otherwise there is a risk that the end might melt or bend. If the end is cooled it should be done in a manner which at least minimizes the risk of calcinations resulting from reaction between different dust particles present in the kiln occurring within the pipe or at the end of the pipe.

Further it is preferred that the cooling is preformed in a manner which prohibits formation of corrosive compounds e.g. reactions products of $SO_2$ or $NO_2$.

In a preferred embodiment of the apparatus the pipe has cooling means for cooling the end of the pipe being introduced into the gaseous medium and more preferred is an embodiment in which the cooling is performed by letting a liquid flow in a cavity In the pipe, preferably the cavity is provided In such a manner that it is unable to reach physical contact with the gaseous medium.

The sample is withdrawn by withdrawing filtered gaseous medium from the outer side of the tubular filter. This results in gaseous medium containing solid particle being transported from e.g. the kiln via the Interior of the pipe to the inner side of the tubular filter. The gaseous medium then passes through the tubular filter leaving the solid particles on the inside of the filter. Preferably the sample is withdrawn by means of a pump and more preferably only the amount of gaseous medium needed for the analyse is withdrawn. Thus the amount of gas passing through the pipe can be heavily reduced. Previously the amount of gas passed through the pipe using continuously flow is in order of 30-40 $m^3/h$, with this new apparatus there is only need for 50-70 l/h and an visual inspection is allowed.

In a preferred embodiment of the invention the tubular filter is attached in the apparatus with an elastic material so as to allow it to expand when heated by the gaseous medium. More preferably the filter is attached by means of at least one O-ring made of an elastic material and even more preferably the filter is attached by means of two O-rings. The O-ring also serves as a gas tight sealing thus securing the no sample gas bypass the filter. By using such an attachment of the filter it is possible to use a variety of filtering material since the person skilled in the art do not have to worry about expansion of the filter. Further this design allows for at larger temperature range in which the apparatus can be used since the filter as mentioned can expand during heating. This is an advantage compared to prior mounting of the filter.

The tubular filter can be made of any conventional filter material. In a preferred embodiment the filter is made of: centred stainless steel, reinforced fibre glass, a porous material or a ceramic material.

In a preferred embodiment inner diameter of the tubular filter has a ratio to the inner diameter of the pipe within the ranges of: 1:1 to 1:5.

Preferably the withdrawal means are in form of a withdrawal port and preferably the blow back means are in form of a blow back port. The advantage of having the blow back port separated from the withdrawal port is that there it solves the problem that occurs when mixing cold cleaning gas with hot sample gas Inside the port. In this case there is a risk of condensation of both water and acid components from the sample gas due to the temperature change of the sample gas when it meets the cold cleaning gas. By using dry cleaning gas in a separate port condensation is avoided.

Even though only a small amount of gas is passed through the tubular filter from time to time is will be necessary to clean the filter. In this new apparatus the cleaning procedure is much easier the previously known procedures. Further with this new procedure a much more powerful cleaning can be obtained. This is a result of having one the straight pipe which secures that the pressure drop is minimal thus all the power in the cleaning blow is used to transport dust out of the pipe.

First a small amount of gaseous medium is passed from the outer side of the tubular filter to the inner side of said filter, thus lifting the filtered of particles from the filter surface. Preferably the gaseous medium is supplied be means of a pump in communication with the outside of the tubular filter e.g. by having a compressor creating a super-pressure in a storage tank and the lead gas from said storage tank to the outside of the filter.

The particles lifted from the filter surface are then carried back into the kiln by a second gas flow, which preferably is provided through the access port and preferably by means of another pump or even more preferably by leading a second gas stream from the previously mentioned storage tank or from a second storage tank to the quick connector of the access port in the removable closure. In a more preferred embodiment the second gas flow is provided by means of a pressure tube.

After this cleaning a visual inspection of the pipe is often desirable. In this new apparatus such an inspection only takes in the order of 2 minutes. The access port is opened and then there is line of sight through the pipe allowing for inspection by looking through the pipe. Previously the pipe arrangement has to be disconnected or the filter has to be removed and operation which takes from 30 minutes up to 2 hours. If necessary it is possible to manually clean the pipe by introducing a rod through the access port and into the pipe thus removing any particulate matter in the pipe.

By using the apparatus according to the invention also a new method is provided i.e. a method for withdrawing a sample of gaseous medium from a gaseous medium containing solid particles comprising the steps of:

withdrawing a sample of gaseous medium through a pipe having one end adapted for introduction into said gaseous medium, a tubular filter for filtering off the solid particles, said filter being positioned coaxially with the pipe and communicating with the interior of the pipe and said pipe having cooling means for cooling the end adapted for introduction into the gaseous medium passing the sample through the tubular filter from the inner side to the outer side for filtering off the solid particles withdrawing the filtered gaseous medium from the outer side of the tubular filter.

Further the apparatus provides a new method for visual inspection of the pipe in an apparatus according to the invention, said method comprising the step of:

opening an access port in a removable closure inspecting the pipe optionally closing the access port in the removable closure Further the invention provides a new method for cleaning an apparatus of the above mentioned kind, the method comprising the steps of introducing a first cleaning gas to the outer side of a tubular filter via separate blow back means passing the cleaning gas from the outer side of the tubular filter to the inner side of the tubular filter introducing a stream of a second cleaning gas coaxially with the axis of the pipe so as to carry particulate matter to the end of the pipe adapted for introduction into the gaseous medium The term separate blow back means it to be understood as means different from those means use to withdraw filtered gas.

In a preferred embodiment the first and the second cleaning gasses are introduced simultaneously.

The first and the second cleaning gasses can be of the same kind or being different, preferably they are the same.

In another preferred embodiment the first and the second cleaning gas are introduced alternatingly.

In the following the invention will be described in further details with reference to the figures.

Figure 1:
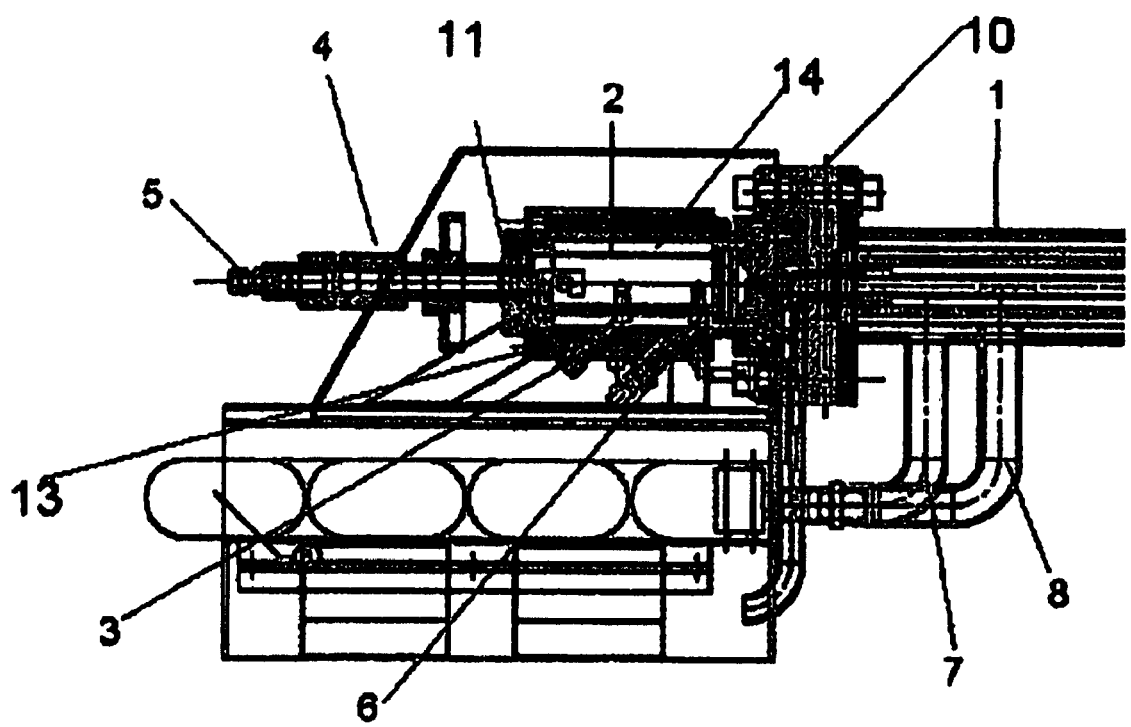
FIG. 1 shows an embodiment of the apparatus according to the invention.

FIG. 1 illustrates an apparatus for taking out a sample of a gaseous medium containing solid particles according to the invention said apparatus comprises a pipe (1) with a coaxially mounted tube-shaped filter (2). On the outside of said tube-shaped filter (2) there are means (3) for sucking out the filtered gas. The tube-shaped filter is mounted in the apparatus by two O-rings (10) which is made of an elastic material. The filtered gas is led to an analyzing chamber (not shown) where the composition of the gas is determined. In the end of the pipe being opposite to the end being introduced into the gaseous medium is a removable closing (11). The removable closing (11) is positioned after the pipe-shaped filter and is placed coaxially with the pipe. The removable closing further comprises an access port (4) positioned coaxially with the pipe and which allows for rapid inspection of the pipe and cleaning if necessary. The access port has connecting means (5) for connecting a pressure tube to the closing, thus providing the option of blowing cleaning gas through the pipe in the opposite direction than the flow direction of the sample being taken out. One of the walls (13) embracing the chamber (14) positioned on the outside of the filter also has means (6) for connecting a gas source to the apparatus. During cleaning, gas is supplied from a gas source via the means (6) to the outside of the filter. The gas is then passed from the outside of the fiber to the inside of the filter and during this passing the solid particles is lifted from the inside surface of the filter and is carried out of the pipe by the cleaning gas flowing through connecting means (5). This embodiment of the apparatus further comprises cooling means for cooling the end of the pipe being introduced into the gaseous medium. A liquid is passed from (7) via at least one cavity in the pipe to the end being introduced into the gaseous medium and back to the exit (8) or visa versa. The cavity in the pipe is made in such a manner that the liquid flowing in the cavity is unable have physical contact with the gaseous medium and/or the sample being taken out i.e. the cavity is adapted to receive a cooling liquid.

Figure 2:
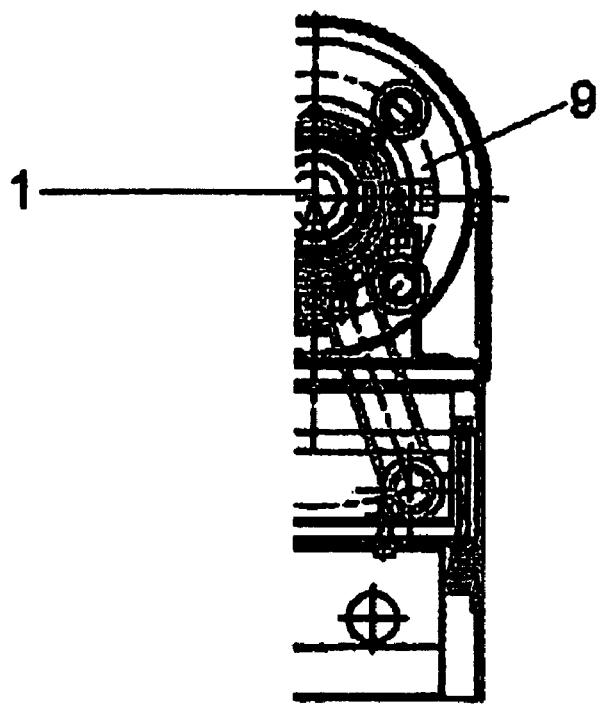
FIG. 2 shows a longitudinally view of the apparatus from the end comprising the removable closing.

In FIG. 2 the apparatus is shown from the end having the removable closing. It can be seen how it is possible to visual Inspection of the pipe (1) since it is strait. Further the cavity (9) for the cooling liquid is illustrated.

Figure 3:
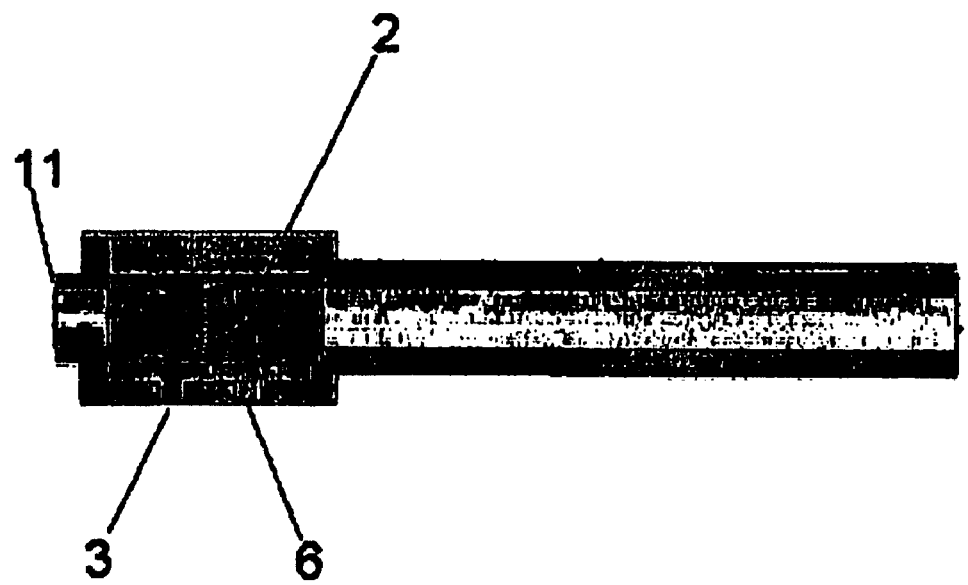
FIG. 3 shows an enlargement of the pipe.
Figure 4:
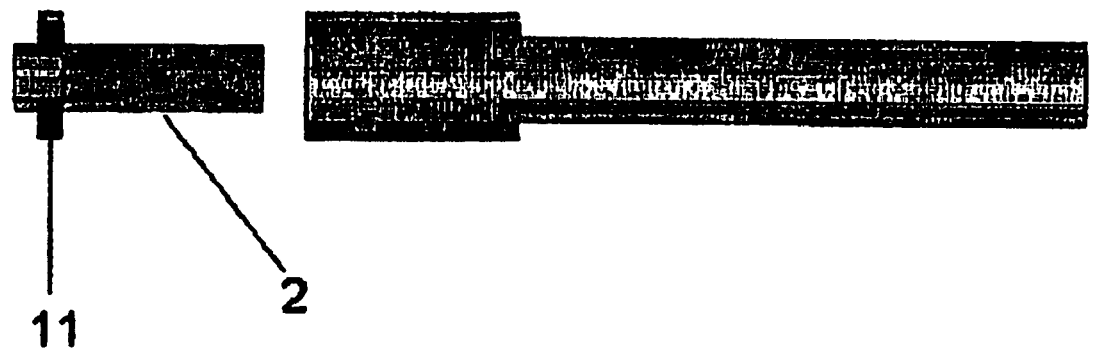
FIG. 4 shows an enlargement of the pipe with the removable closure removed.

In FIG. 3 the pipe is enlarged. The pipe-shaped filter (2) is attached to the removable closure (11) and as can be seen in FIG. 4 the pipe-shaped filter can be removed along with the removable closure.

Figure 5:
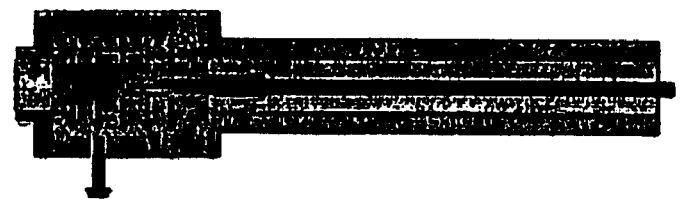
FIG. 5 shows the mechanism of taking out gaseous samples.

FIG. 5 illustrates how the gaseous medium containing solid particles passes through the pipe to the filter, which the gaseous medium passes leaving the solid particles on the inner side of the filter and that the filtered gas is withdrawn from the outside.

Figure 6:
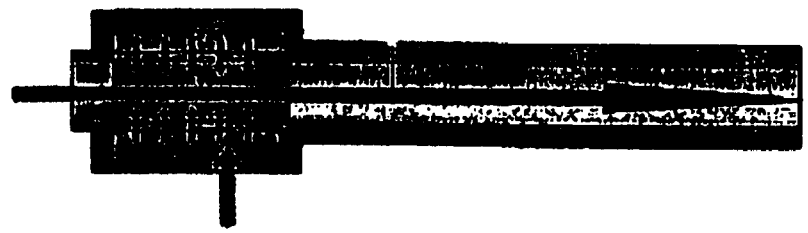
FIG. 6 shows the mechanism of cleaning.

FIG. 6 illustrates the cleaning procedure In which gas is blown from the outside of the filter, through the filter lifting off the filter off particles. The lifter particles in then carrier out of the pipe by a second gas flow.

The invention claimed is:

1. A method for cleaning an apparatus for taking samples of a gaseous medium containing solid particles, the apparatus comprising:

a pipe having one end adapted for introduction into the gaseous medium, a tubular filter for filtering off the solid particles that is positioned coaxially with the pipe and communicates with the interior of the pipe, a removable closure positioned on the downstream side of the tubular filter and coaxially with the pipes withdrawal means for withdrawing the filtered gaseous medium from the outer side of the tubular filter, and separate blow back means in communication with the outer side of the tubular filter, said method comprising the steps of:

discontinuing withdrawal of gaseous medium by the withdrawal means from the outside of the tubular filter;

introducing a first cleaning gas to the outer side of the tubular filter via the separate blow back means after withdrawal of the gaseous medium has been discontinued;

passing the cleaning gas from the outer side of the tubular filter to the inner side of the tubular filter; and introducing a stream of a second cleaning gas coaxially with the axis of the pipe so as to carry particulate matter to the end of the pipe adapted for introduction into the gaseous medium.

2. A method according to claim 1, wherein the removable closure comprises an access port positioned coaxially with the pipe.

3. A method according to claim 1, wherein the pipe has cooling means for cooling the end adapted for introduction into the gaseous medium.

4. A method according to claim 1, wherein the apparatus further comprises at least one connecting means for connecting the apparatus to a gas source.

5. A method according to claim 2, wherein the access port has connecting means for connecting the apparatus to a gas source.

6. A method according to claim 1, wherein the separate blow back means is positioned in one of the walls embracing a chamber on the outside of the filter.

7. A method according to claim 1, wherein the access port and one of the walls embracing the chamber on the outside of the filter has means for connecting the apparatus to a gas source.

8. A method according to claim 1, wherein the pipe has at least one cavity adapted to receive a cooling liquid.

9. An apparatus for taking samples of a gaseous medium containing solid particles, said apparatus comprising:

a pipe having one end adapted for introduction into said gaseous medium, a tubular filter for filtering off the solid particles that is positioned coaxially with the pipe and communicating with the interior of the pipe, a removable closure being positioned on the downstream side of the tubular filter and coaxially with the pipe, the closure comprising an access port positioned coaxially with the pipe and adapted for introduction of cleaning gas, withdrawal means for withdrawing the filtered gaseous medium from the outer side of the tubular filter, and a separate inlet for supplying cleaning gas under pressure, said separate inlet being in communication with the outer side of the tubular filter.

\* \* \* \* \*